US00PP10107P

United States Patent [19]

Trees

[11] Patent Number: Plant 10,107

[45] Date of Patent: Nov. 4, 1997

[54] NEW GUINEA IMPATIENS NAMED 'GRAPE CRUSH'

[75] Inventor: Scott C. Trees, Arroyo Grande, Calif.

[73] Assignee: Ball Horticultural Company, West Chicago, Ill.

[21] Appl. No.: 685,535

[22] Filed: Jul. 24, 1996

[51] Int. Cl.[6] ..... A01H 5/00

[52] U.S. Cl. ..... Plt./87.6

[58] Field of Search ..... Plt./87.6

[56] References Cited

PUBLICATIONS

GTITM LIPOVROM Listing for CA PBR 96–904 for 'Grape Crush' from application filed Jul. 5, 1996, Oct. 31, 1997.

*Primary Examiner*—James R. Feyrer

*Attorney, Agent, or Firm*—Burns, Doane, Swecker & Mathis, L.L.P.

[57] ABSTRACT

A new and distinct New Guinea Impatiens cultivar named 'Grape Crush' is provided. This new cultivar was the result of a controlled breeding program wherein the 'Papete' cultivar (U.S. Plant Pat. No. 8,457) was pollinated by the 'Tahiti' cultivar (U.S. Plant Pat. No. 8,601). The new cultivar forms large round rich purple flowers with a red eye that display an iridescent appearance. The foliage is medium green in coloration. An attractive moderately compact upright mounded growth habit is exhibited. The new cultivar can be readily distinguished from the parent 'Papete' cultivar.

1 Drawing Sheet

SUMMARY OF THE INVENTION

The present invention comprises a new and distinctive Impatiens plant, botanically known as New Guinea Impatiens, and hereinafter is referred to by the cultivar name 'Grape Crush'.

The new cultivar is the product of a planned breeding program. More specifically, the breeding program which resulted in the production of the new cultivar was carried out in a controlled environment during 1992 at Arroyo Grande, Calif., U.S.A. The female parent (i.e., the seed parent) was the 'Papete' cultivar (U.S. Plant Pat. No. 8,457) which exhibits purple blossoms, dark green foliage, and a compact growth habit. The male parent (i.e. the pollen parent) was the 'Tahiti' cultivar (U.S. Plant Pat. No. 8,601) which exhibits light pink blooms, dark green foliage, and a compact growth habit. The parentage of the new cultivar can be summarized as follows:

'Papete' × 'Tahiti'.

The seeds resulting from the above pollination were sown and plantlets were obtained which were physically and biologically different from each other. Selective study resulted in the identification of a single plant of the new cultivar. This plant initially was designated BFP-607.

It was found that the new cultivar of the present invention:

(a) exhibits attractive large round vibrant purple flowers with a red eye,
(b) forms medium green foliage,
(c) exhibits a good basal branching character, and
(d) exhibits a moderately compact upright growth habit.

The new cultivar blooms early and continuously. Plants of the new cultivar can be grown close together in the greenhouse.

Asexual reproduction of the new cultivar by terminal or stem cuttings taken during 1994, at Arroyo Grande, Calif., U.S.A. has demonstrated that the characteristics of the new cultivar as herein described are firmly fixed and are retained through successive generations of such asexual propagation.

The 'Grape Crush' cultivar has not been observed under all possible environmental conditions to date. Accordingly, it is possible that the phenotype may vary somewhat with variations in the environment, such as temperature, light intensity, and day length.

When the new cultivar of the present invention is compared to the parent 'Papete' cultivar (U.S. Plant Pat. No. 8,457), it is found that the new variety is more floriferous, has slightly smaller flowers, and bears leaves that are more yellow in coloration.

Plants of the new cultivar are marketed under the CELEBRETTE trademark by the Ball Horticultural Company.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at West Chicago, Ill., U.S.A.

DETAILED DESCRIPTION

The chart used in the identification of colors described herein is the R.H.S. Colour Chart of The Royal Horticultural Society, London, England. The plants were produced from cuttings taken from stock plants of the new cultivar and were transplanted during early November into 10 cm. (4 inch pots) and were grown in a soilless growth medium under standard greenhouse conditions at West Chicago, Ill., U.S.A. The greenhouse temperature was maintained at approximately 72° F. during the day and approximately 65° F. during the night. The plants were in flower eight to nine weeks later when the observations described hereafter were taken.

Botanical classification: *Impatiens hawkeri*.

Propagation:

*Type cutting*.—Terminal tip.

*Time to initiate roots.*—Approximately 14 to 21 days with the shorter times generally being experienced in the summer and the longer times in the winter.

*Rooting habit.*—Fibrous, and branching.

Plant description:

*Form.* —Basal branching.

*Habit of growth.*—Moderately compact, and upright mounded. Internode lengths of approximately 2.5 to 2.8 cm. commonly are exhibited. A mature plant commonly measures approximately 8 to 9 cm. in height and approximately 20 to 23 cm. in width. This compares to a height of approximately 8 to 9 cm. and a width of approximately 16 to 20 cm. for the parent 'Papete' cultivar.

*Foliage.* —The configuration is elliptic with an acuminate apex and an acuminate base. The mature leaves of the new cultivar measure approximately 9 to 10 cm. in length × approximately 3 to 3.7 cm. in maximal width compared to approximately 9.5 to 10.5 cm. in length × approximately 4 to 4.5 cm. in maximal width for the 'Papete' cultivar. The leaf margins are serrate (as illustrated). The mature foliage of new cultivar is Green Group 139A (adaxial) and Green Group 138A (abaxial). This compares to Yellow-Green Group 147A (adaxial) and Greyed-Green Group 191A (abaxial) for the parent 'Papete' cultivar.

Flower description:

*Flowering habit.*—Freely flowering.

*Natural flowering season.*—Throughout the year in a greenhouse environment.

*Flowers borne.*—Above foliage, arising from leaf axils.

*Flower color.*—The petals are brighter than Red-Purple Group 74A with the lower four petals commonly displaying bases of Red Group 53C (adaxial), and Red-Purple Group 74B (abaxial). This compares to darker than Red-Purple Group 74A (adaxial), and Red-Purple Group 74B (abaxial) for the present 'Papete' cultivar.

*Quantity of flowers.*—Approximately 6 to 7 per axial which can be compared to approximately 4 to 5 per axial for the parent 'Papete' cultivar.

*Number of petals.*—Five, and overlapping.

*Petal shape.*—Somewhat heart-shaped but not as regular as the parent 'Papete' cultivar, with the superior petal having a broad base and the other petals having generally pointed bases.

*Flower size.*—Approximately 5.3 to 6.0 cm. in length and approximately 5.3 to 6.0 cm. in width. This can be compared to approximately 5.9 to 6.2 cm. in length and approximately 5.9 to 6.2 cm. in width for the parent 'Papete' cultivar.

*Flower buds.*—Ellipsoidal in configuration, and generally covered with three sepals plus two rudimentary sepals fused into the under surface of the superior petal. A spur originating from the base of the inferior sepal is approximately 5 to 6 cm. in length on fully opened flowers which can be compared to approximately 6 to 7 cm. for the spur of the parent 'Papete' cultivar. The spur coloration is Red-Purple Group 60A. This compares to a spur coloration of Red Group 53A for the parent 'Papete' cultivar.

*Reproductive organs.*—The stamens are Red-Purple Group 74B for both the new cultivar and the parent 'Papete' cultivar. The anthers tend to be fused together forming one organ that surrounds the pistil. Commonly the anthers shed pollen prior to the stigma becoming receptive. The pollen coloration is Yellow Group 11B and the ovary coloration is Yellow-Green Group 144A for both the new cultivar and the parent 'Papete' cultivar.

I claim:

1. A new and distinct cultivar of New Guinea Impatiens plant named 'Grape Crush', substantially as herein shown and described, which:

(a) exhibits attractive large round vibrant purple flowers with a red eye, (b) forms medium green foliage, (c) exhibits a good basal branching character, and (d) exhibits a moderately compact upright growth habit.

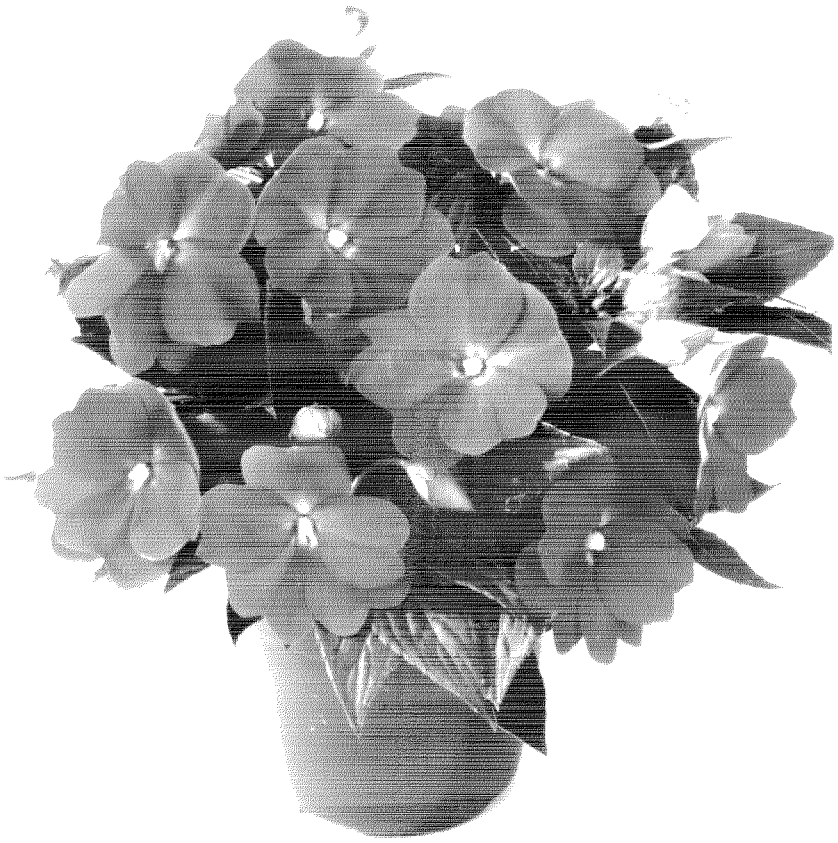

* * * * *